United States Patent [19]

Meserol et al.

[11] Patent Number: 5,029,583

[45] Date of Patent: Jul. 9, 1991

[54] OPTICAL ANALYZER

[75] Inventors: Peter M. Meserol, Montville; Thomas Palmieri, Paramus, both of N.J.

[73] Assignee: Personal Diagnostics, Inc., Whippany, N.J.

[21] Appl. No.: 431,914

[22] Filed: Nov. 6, 1989

Related U.S. Application Data

[63] Continuation-in-part of Ser. No. 325,390, Mar. 20, 1989, abandoned, which is a continuation of Ser. No. 219,712, Jul. 15, 1988, abandoned, which is a continuation of Ser. No. 888,754, Jul. 22, 1986, abandoned.

[51] Int. Cl.$^5$ ............................................... A61B 17/3
[52] U.S. Cl. .................................. 128/633; 128/637; 128/763; 128/770; 604/157; 606/182
[58] Field of Search ............... 128/633, 634, 637, 749, 128/751-755, 763, 770; 604/156, 157, 194; 606/181, 182

[56] References Cited

U.S. PATENT DOCUMENTS

| | | | |
|---|---|---|---|
| 2,818,852 | 1/1958 | Kugler | 128/755 |
| 3,692,020 | 9/1972 | Schied | 128/755 |
| 4,517,978 | 5/1985 | Levin et al. | 606/182 |
| 4,545,382 | 10/1985 | Higgins et al. | 128/635 |
| 4,637,403 | 1/1987 | Garcia et al. | 128/637 |

Primary Examiner—Stephen C. Pellegrino
Assistant Examiner—David Shay
Attorney, Agent, or Firm—R. Gale Rhodes, Jr.

[57] ABSTRACT

An optical analyzer for determining an analyte in a fluid of interest such as a body fluid of interest satisfying the foregoing need and embodying the present invention may include a housing; combination optically transparent cuvette and lancet mounted removably in the housing, the cuvette may receive an optically transparent reagent test system for reacting with the body fluid to produce a change in at least one optical transmissive characteristic of the system indicative of the analyte; a cuvette carrier mounted slidably in the housing and for removably receiving the cuvette; a spring actuator mounted in the housing and connected to the cuvette carrier, the spring actuator may be compressed and released to advance the carrier and thereby advance the lancet into engagement with a portion of a body to produce the body fluid; depth control apparatus for controlling the depth of penetration of the lancet into the body portion; an electrooptical system mounted in the housing in optical engagement with the cuvette and for passing a light beam through the cuvette and the reagent system and for receiving the light beam modified by the change in optical transmissive characteristic of the system and for transmitting computation signals indicative of the analyte to a computer; a computer mounted in the housing for receiving the computation signals and for comparing the computation signals against predetermined data to produce display signals indicative of the analyte; a display mounted in the housing and for receiving the display signals and for providing a vehicle display indicative of the analyte; and control switches mounted in the housing and connected to the computer for controlling the operation of the computer.

5 Claims, 6 Drawing Sheets

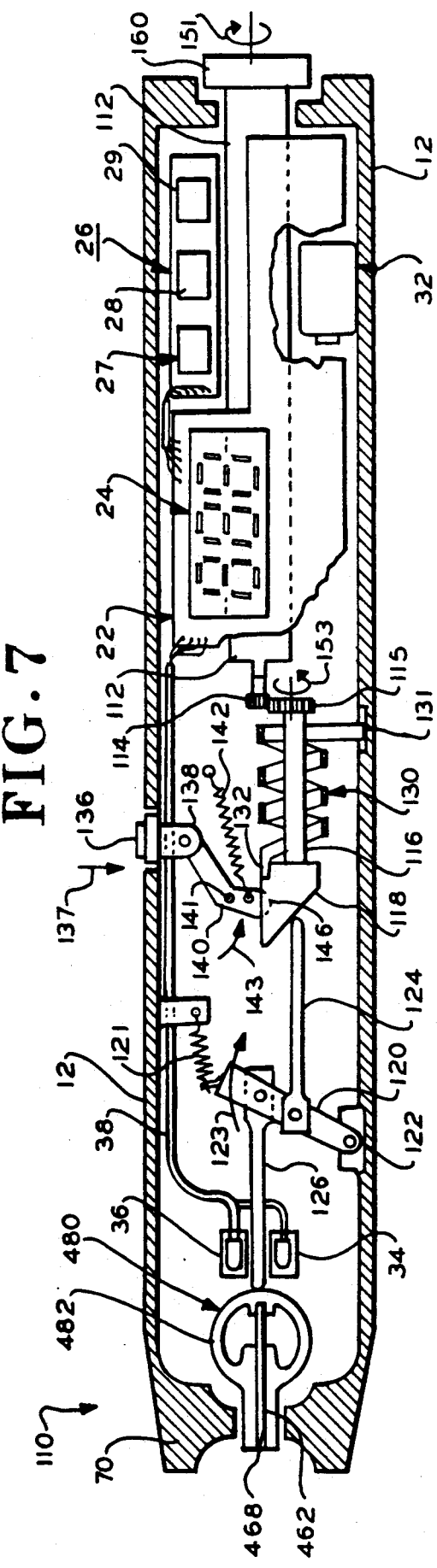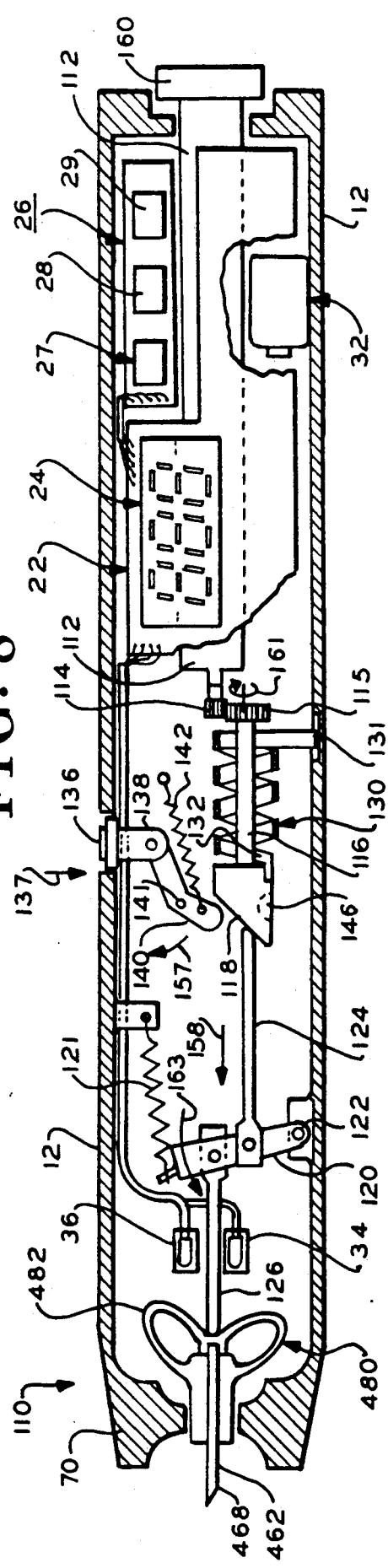

OPTICAL ANALYZER

Cross Reference to Related Applications

This application is a continuation-in-part of abandoned United States patent application Ser. No. 325,390, filed Mar. 20, 1989, entitled OPTICAL ANALYZER, Peter M. Meserol et al. inventors, which application is a continuation of abandoned United States patent application Serial No. 007/219,712, filed July 15, 1988, entitled OPTICAL ANALYZER, Peter M. Meserol et al. inventors, which application is a continuation of abandoned United States patent application Ser. No. 06/888,754, filed July 22, 1986, Peter M. Meserol et al. inventors.

BACKGROUND OF THE INVENTION

This invention relates generally to a new and improved optical analyzer for determining analyte in a fluid of interest, and more particularly relates to a new and improved miniaturized optical analyzer for determining analyte in a body fluid of interest and which analyzer is of sufficiently small size and weight to permit the optical analyzer to be taken to the source of the analyte body fluid such as a patient in a hospital bed or a home user.

The term "analyte" as known to those skilled in the art is a term or expression used to identify generally something that is determined by analysis as to its presence, the amount present, etc. For example, the amount of blood glucose present in blood is determined by diabetics to monitor the amount of insulin to be taken or to determine whether or not additional insulin should be taken; hence, it will be understood that in this context the "analyte" is blood glucose.

As further known to those skilled in the art, numerous optical analyzers are known for determining analytes in many different fluids of interest such as body fluids, e.g. blood, urine, saliva, etc. Many of such prior art optical analyzers are of such optical complexity size and weight, and have energy requirements such that they must be mounted stationary whereby the body fluid of interest must be taken from the source, such as a patient in a hospital bed or a patient coming to a doctor's office, whereafter the body fluid must be transmitted distantly to the location of the stationary optical analyzer for determination. While this procedure generally has worked well, it is known that the time lost between obtaining the fluid of interest, such as blood from a patient and transmitting the fluid distantly to the location of the stationary optical analyzer, may result in some deterioration of the fluid and thus some loss of quality in the subsequent analysis and analyte determination.

Accordingly, there exists a need in the art for an optical analyzer of sufficiently small size and weight whereby the optical analyzer is portable and may be, for example, taken to a patient in a hospital bed or purchased and taken home for home use.

SUMMARY OF THE INVENTION

An optical analyzer for determining an analyte in a fluid of interest such as a body fluid of interest satisfying the foregoing need and embodying the present invention may include a housing; combination optically transparent cuvette and lancet mounted removably in the housing, the cuvette may receive an optically transparent reagent test system for reacting with the body fluid to produce a change in at least one optical transmissive characteristic of the system indicative of the analyte; advancing means for advancing advance the lancet out of the housing and into engagement with a portion of a body to produce the body fluid; depth control apparatus for controlling the depth of penetration of the lancet into the body portion; an electro optical system mounted in the housing in optical engagement with the cuvette and for passing a light beam through the cuvette and the reagent system and for receiving the light beam modified by the change in optical transmissive characteristic of the system and for transmitting computation signals indicative of the analyte to a computer; a computer mounted in the housing for receiving the computation signals and for comparing the computation signals against predetermined data to produce display signals indicative of the analyte; a display mounted in the housing and for receiving the display signals and for providing a visible display indicative of the analyte; and control switches mounted in the housing and connected to the computer for controlling the operation of the computer.

BRIEF DESCRIPTION OF THE DRAWINGS

FIGS. 7 and 8 are similar to FIG. 2 but illustrate an alternate embodiment of an optical analyzer embodying the present invention.

DESCRIPTION OF THE PREFERRED EMBODIMENT

Referring now to the FIGS., an optical analyzer embodying the present invention and indicated by general numerical designation 10 is illustrated. In the following description, the optical analyzer 10 will be described as embodied as an optical analyzer for determining the amount of glucose in human blood, but it will be expressly understood by those skilled in the art that the present invention is not so limited and has a wide variety of analyte determination applications. For example, and not by way of limitation, the optical analyzer of the present invention may be also used to determine cholesterol, blood urea nitrogen, etc.

Figure 1:
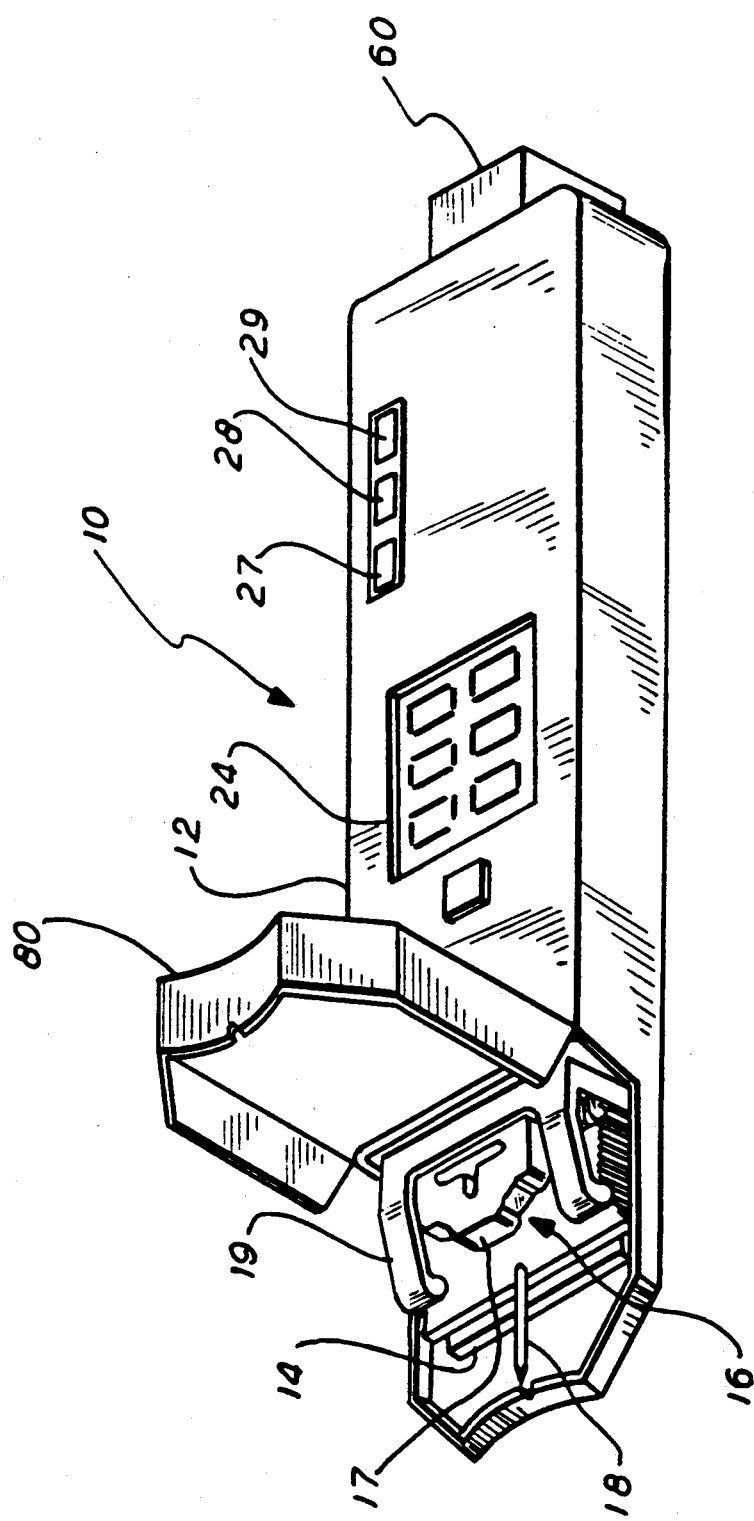
FIG. 1 is a perspective view of an optical analyzer embodying the present invention.

The optical analyzer 10 may include a housing 12 in which is slidably mounted a cuvette carrier 14 for removably receiving a disposable combination cuvette and lancet indicated by general numerical designation 16 with the cuvette being indicated by individual numerical designation 17 and with the lancet being indicated by individual numerical designation 18; the cuvette carrier 14 may include a clamp 19, FIG. 1, for removably clamping the cuvette 17 to the carrier. Combination cuvette and lancet 16 may be the IMPROVED CUVETTE embodiment of FIG. 1 disclosed in U.S.

Figure 2:
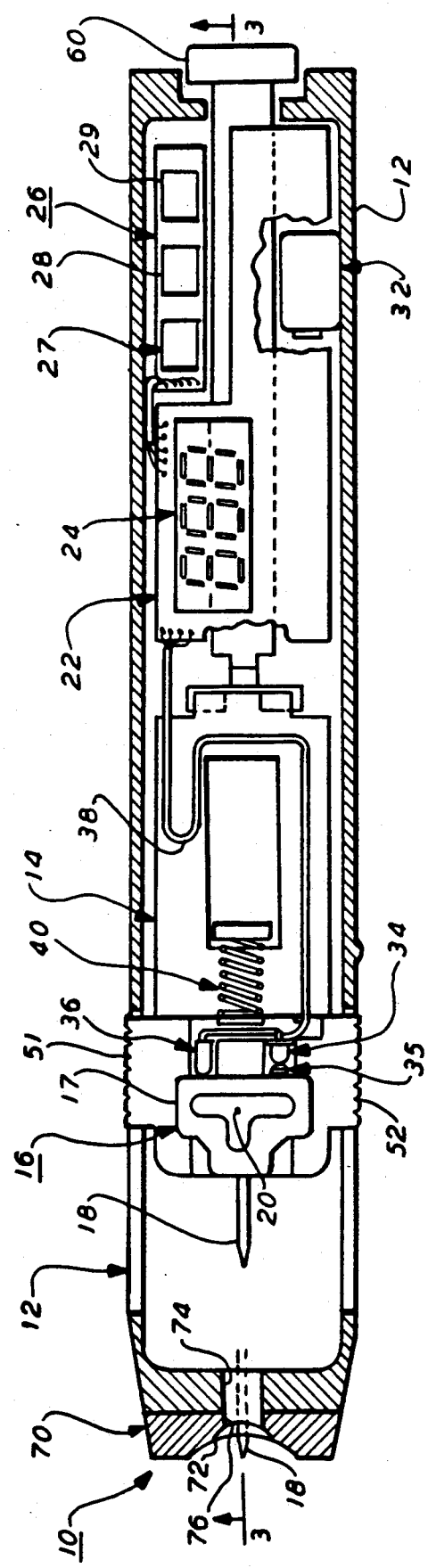
FIG. 2 is a plan view, in partial cross-section and with the top portion of the housing removed, showing the optical analyzer embodying the present invention.

Pat. No. 4,873,393, issued Oct. 17, 1989, Peter M. Meserol et al. inventors, and assigned to the same assignee as the present invention; such patent is hereby incorporated herein by reference as if fully reproduced herein. As illustrated in FIG. 2, the cuvette 17 is generally T-shaped in plan and is provided at the top with a T-shaped opening 20. As taught in the above-identified IMPROVED CUVETTE application, cuvette 17 may be filled with an optically transparent gel including a test reagent system for determining the amount of glucose present in human blood by a color change upon reaction of the blood, or a sample portion thereof, with the test reagent system which color change produces a change in the optical transmissive character of the gel and test reagent system contained within the cuvette 17; the optically transparent gel and test reagent system may be the blood glucose assay disclosed in United States patent application Ser. No. 06/876,473, filed June 20, 1986, entitled ASSAY SYSTEM IN GEL MATERIAL, Rita C. Prodell et al. inventors, and assigned to the same assignee as the present invention. Accordingly, it will be assumed that the cuvette 17 has been filled with such optically transparent gel and test reagent system.

A computer 22 is mounted in the housing 12 and is connected to a display 24, for example by suitable surface mount technology in the manner known to those skilled in the art. Also connected to the computer 22, as shown, is a control panel indicated by general numerical designation 26 and including a calibrate button 27, a test button 28, and a memory button 29. A power supply, such as battery 32, is included to provide energy for operating the optical analyzer 10. A photoemitter 34, and collimating lens 35 if desired or required, and a photodetector 36, in optical engagement with the cuvette 17 are provided for passing a beam of light through the cuvette and the gel and test reagent system contained therein and for receiving the light beam modified by the above-noted change in optical transmissive characteristic of the gel and test reagent system and for transmitting computation signals over the flexible line 38 to the computer 22.

Figure 3:
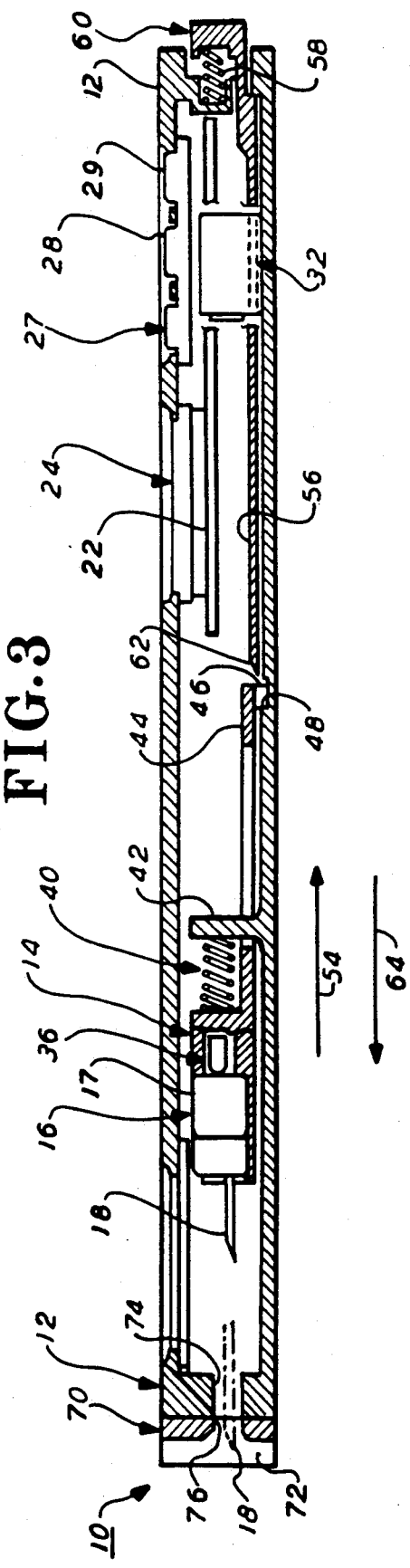
FIG. 3 is an irregular side view in elevation taken generally along the line 3—3 in FIG. 2.

Spring 40 is mounted within the housing between the cuvette carrier 14 and the member 42 formed, for example, integrally with the housing 12 as illustrated in FIG. 3. As is further shown in FIG. 3, the rearward portion 44 of the cuvette carrier 14 is provided with a pair of downwardly extending, spaced apart detent members, only member 46 being shown in FIG. 3, for engaging the vertically upwardly extending portion 48 of the housing 12 upon the operator engaging the cuvette carrier 14, particularly the serrated portions 51 and 52 shown in FIG. 2, and forcing the cuvette carrier rearwardly in the direction of the arrow 54 of FIG. 3 to also compress the spring 40. A release lever 56 may be spring mounted in the housing 12, by spring 58 as shown, and may include a rearward release button 60 which upon being forced inwardly into the housing causes a camming portion 62 provided at the forward portion of the release lever 56 to engage the rearward portion 44 of the cuvette carrier 14 forcing the rearward portion upwardly to release the detent member 46 from the housing portion 48 whereupon the spring 40 advances the cuvette carrier and with it the combination cuvette and lancet 16 forwardly in the direction of the arrow 64 of FIG. 3 and to advance the lancet 16 into the forward positions shown in dashed outline in FIGS. 2 and 3 to puncture the finger of the user to a predetermined depth to produce a wound from which blood will flow. The depth of puncture may be controlled by the thickness of a tip 70 provided at the forward end of the housing and suitably secured thereto such as by a suitable adhesive. As shown in FIGS. 2 and 3, the tip 70 may be provided with an inwardly curved portion 72 to facilitate proper placement of the operator's finger at the forward portion of the optical analyzer 10 for puncture and production of blood. As shown in FIGS. 2 and 3, the tip 70 and the forward portion of the housing 12 are provided with coaxially aligned apertures 74 and 76 through which the lancet 18 may be advanced or extended.

It will be further understood by those skilled in the art that the spring 40 also retracts the cuvette carrier 14 and with it the cuvette 17 and lancet 18 to retract the lancet 18 within the housing 12 to prevent unwanted injury by the lancet. This retraction is accomplished by providing the slide carrier 14 with sufficient mass such that upon the spring 14 being compressed and the carrier released, the cuvette carrier will be forced forwardly sufficiently far to advance the lancet for finger puncture as described but also farther than the length of normal extension of the spring whereupon the spring will be placed in tension and will thereafter contract and retract the carrier slide and with it the cuvette and lancet as described.

The finger blood will be wiped across the T-shaped opening 20 of the cuvette 17 and will enter the cuvette and react with the test reagent system included in the gel contained therein, as described above, to cause a change in at least one optical transmissive characteristic of the gel and test reagent system, such as for example a change of color therein. The photoemitter 34 will pass a beam of light through the cuvette and the gel and test reagent system contained therein and the beam of light will be modified by the change in optical transmissive characteristic of the gel and test reagent system and the modified light beam will be received by the photodetector 36 which will transmit computation signals over the flexible line 38 to the computer 22. The computer will compare the computation signals against stored data to produce and transmit to the display 24 display signals indicative of the amount of glucose present in the blood, and the display will provide a digital display indicative thereof.

Referring again to FIG. 1, it will be noted that the upper portion of the housing 12 may be provided with a hinged or pivotally mounted portion 80 which may be pivoted upwardly, as shown in FIG. 1, to permit loading of the combination cuvette and lancet 16 into the optical analyzer 10 and which may thereafter be closed to operate the optical analyzer 10 as described above to puncture a finger to produce blood particularly a droplet of blood. Thereafter, the hinged portion 80 may again be pivoted upwardly as shown in FIG. 1 to permit the blood to be wiped across the T-shaped cuvette opening 20 to permit the blood to enter the cuvette and the plasma to diffuse into and react with the test reagent system included in the optically transparent gel, as described above.

Figure 4:
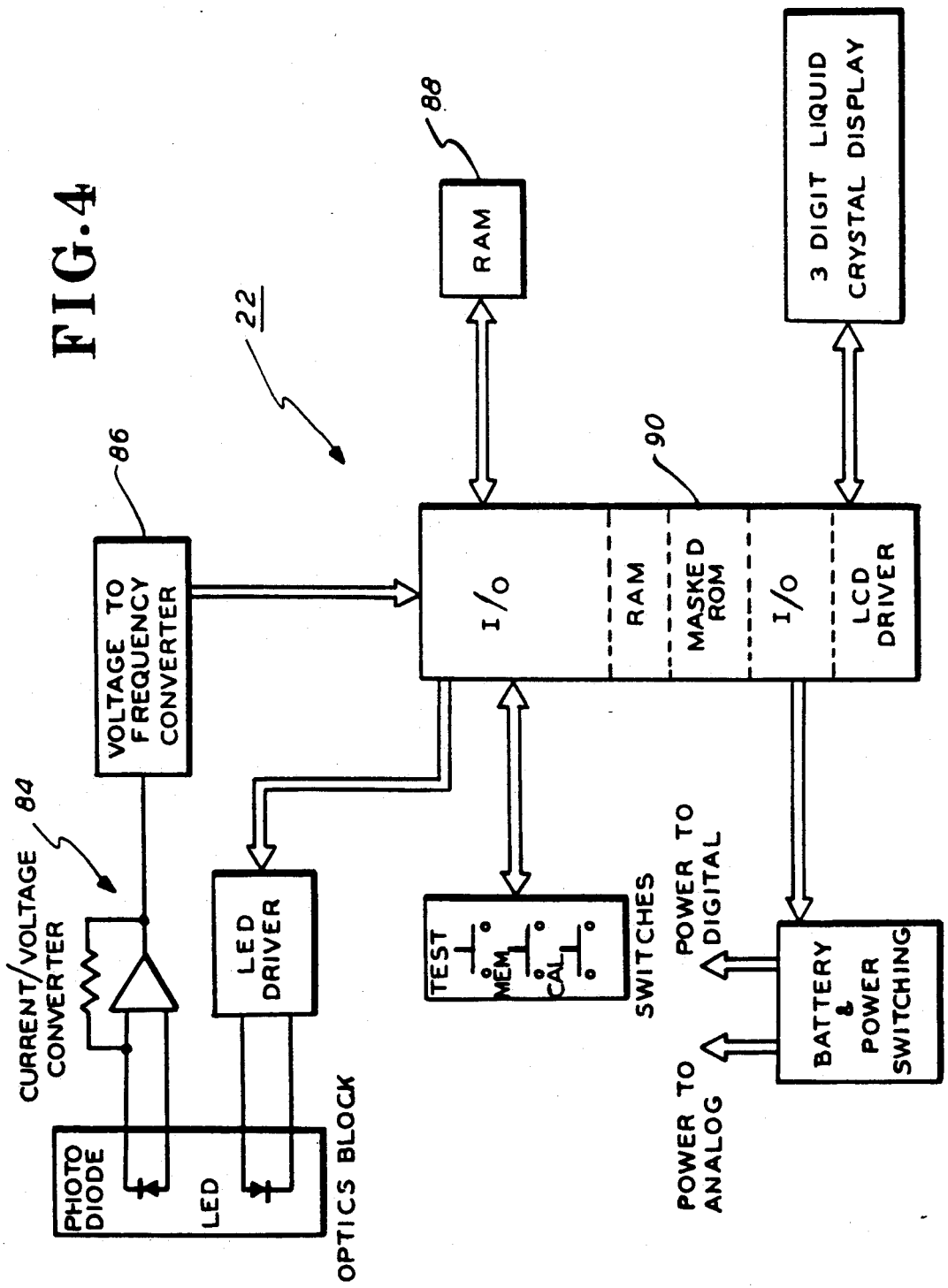
FIG. 4 is a general block diagram of an electrical circuit which may be embodied in a computer included in the optical analyzer of the present invention.

Referring now to FIG. 4, there is illustrated a block diagram of the computer 22 and, as noted generally above, it will be understood that the optical analyzer 10 of the present invention has three different modes of operation, namely test, calibrate and memory. It will be assumed that the operator, or patient, has produced a sample of blood and the blood has been wiped across the cuvette opening 20 and the plasma has entered and diffused into the gel and reacted with the test reagent system included therein, as described above. The operator then closes the pivotal member 80 (FIG. 1) and depresses the test key 28. The computer 22 then applies voltage to the circuitry and to the photoemitter 34 (FIG. 2) to generate and pass a beam of light into and through the cuvette 17 and the gel and test reagent system contained therein undergoing a change in at least one optical transmissive characteristic as noted above. The modified light beam is then received by the photodetector 36 (FIGS. 2 and 3) which generates a photocurrent proportional to the intensity of the light beam received. This current is amplified and converted to a voltage by the current-to-voltage converter 84 of FIG. 4; thereafter, the voltage is converted to a square wave at a frequency proportional to the applied voltage by the voltage-to-frequency converter 86. The computer 22 then determines the frequency of the square wave at fixed or predetermined intervals over the predetermined period of the test. Using this data, the computer 22 calculates the optical density change in the gel and test reagent system and determines the maximum rate of change of the test reagent system in the cuvette. Once this determination is made, the rate is equated to a blood glucose level stored in the computer memory and is thereafter displayed digitally by the display 24 and also stored in memory. Thereafter, the computer 22 automatically turns off and awaits the depression or closure of another switch.

Upon depression of the calibration key 27, the computer 22 functions in the same manner as the above-described test mode except that the sample placed in the cuvette 17 is not unknown blood from a patient but a sample of known glucose concentration to maintain the optical analyzer 10 in proper calibration.

Depression of the memory switch or button 29 permits the patient or user to display stored glucose readings; in one embodiment of the present invention one month's readings can be stored in the RAM 88 of FIG. 4.

As known to those skilled in the art, the computer 22 may consist of surface mounted components or may be incorporated into a suitable chip.

Figure 5:
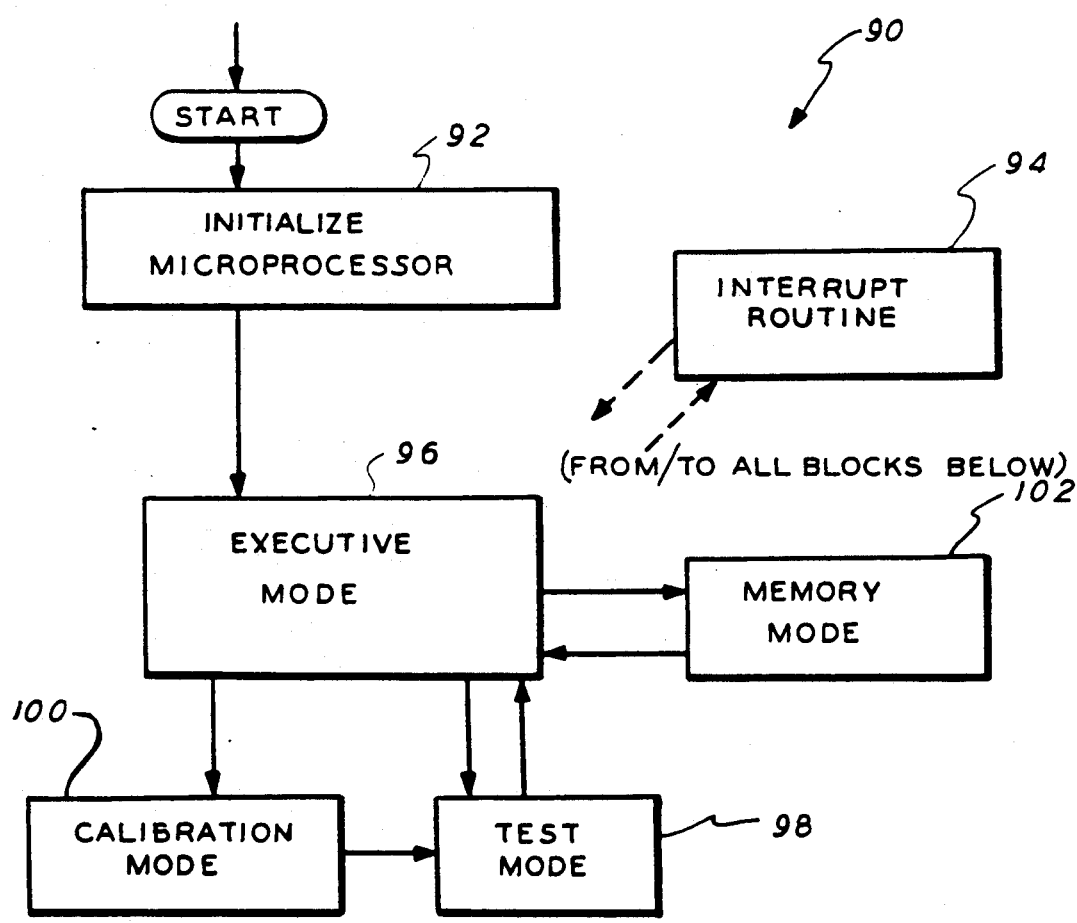
FIG. 5 is a block diagram of a computer program which may be embodied in the computer.
Figure 6:
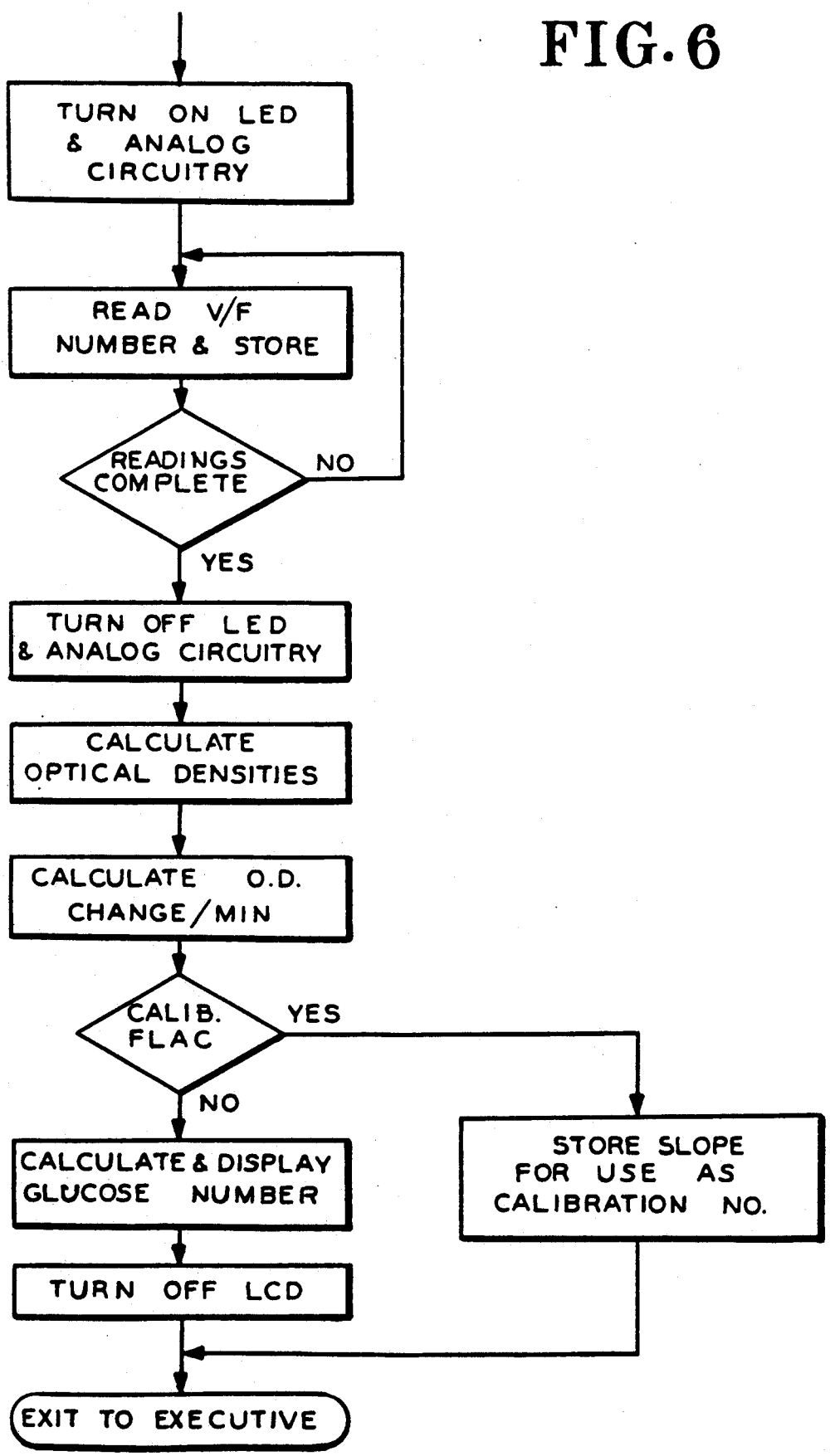
FIG. 6 is a flow chart of the test mode of the computer program.

With regard to the computer software, it will be understood that the controlling element in the computer or microprocessor 22 (FIG. 4), in one embodiment of the present invention, was an eight bit CMOS masked ROM, e.g. ROM 90, and the stored computer program was configured into six basic blocks as illustrated in FIG. 5. Referring first to the initialization mode, block 92, this mode configures the computer control registers, sets timers and clock, clears the memory, and operates other test functions to allow the computer to perform the above-described test function. The interrupt mode, block 94, provides a routine which interrupts the main routine at a predetermined rate to perform the following functions: read the keys or switches 27, 28, and 29, start/stop the voltage to frequency converter 86 (FIG. 4), service the real time clock routine and decrement the test timers and counters. The executive mode, block 96, has the basic function of directing the computer program to the correct mode when one of the keys or buttons, 27, 28 or 29, is depressed. The test mode, block 98, is the primary function of the optical analyzer 10, and a computer or microprocessor 22, and illustrated in FIG. 6 is a flow chart of the test mode computer program; it will be understood by those skilled in the art that the flow chart of FIG. 6 will enable a computer programmer of ordinary skill to program the computer in any one of several different computer programming languages to cause the optical analyzer of the present invention to operate and perform analyte determination, such as the amount of glucose present in blood, as taught above. The calibration mode, block 100, is substantially the same as the test mode except that no blood glucose amount or level is displayed and, as noted above, the calibration mode is run with a known glucose sample to maintain the optical analyzer 10 in proper calibration. Lastly, the memory mode, block 102, allows the patient or operator of the optical analyzer 10 to have access to the memory, RAM 88 of FIG. 4, to display glucose levels or amounts previously stored; when a test is run, the glucose level or amount is stored in this memory as described above.

Referring now to FIGS. 7 and 8, there is illustrated an alternate embodiment of an optical analyzer embodying the present invention which alternate embodiment is indicated by general numerical designation 110. For convenience of reference and understanding, structure in FIGS. 7 and 8 identical to that of optical analyzer 10 shown in FIGS. 2 and 3 described above is given the same numerical designations. It will be understood that alternate embodiment optical analyzer 110 is also embodied as an optical analyzer for determining the amount of glucose in human blood but it will be expressly understood by those skilled in the art that alternate embodiment 110 is not so limited and has a wide variety of analyte determination applications as was noted above with regard to optical analyzer 10. However, as embodied as an optical analyzer for determining the amount of glucose in human blood, it will be understood that the teachings above and the illustrations of FIGS. 4, 5 and 6 as to operability and function of optical analyzer 10 are equally applicable with regard to alternate embodiment opticalanalyzer 110 and will not be repeated; only the differing structure for advancing the lancet will be described below.

It will be further specifically understood that the optical analyzer alternate embodiment 110 is not for use with the disposable combination cuvette and lancet indicated by general numerical designation 16 in FIGS. 2 and 3 but instead is for use with, and for removably receiving, the disposable combination of cuvette and lancet 410 shown in FIG. 22 of above incorporated U.S. Pat. No. 4,873,993 but that for clarity of illustration only the lower member 480 (shown in FIG. 23 of the incorporated patent) of disposable combination cuvette and lancet 410 is shown in FIGS. 7 and 8. The component parts of the lower member 480 shown in FIG. 23 of the incorporated patent, i.e. resilient rearward portion 482, lancet 462 and lancet tip 464 are given the same numerical designations in FIGS. 7 and 8 for convenience of reference and understanding. Still more particularly, it will be understood that the lancet advancing means of the alternate embodiment 110 is for developing and providing the force indicated by arrow 550 in FIG. 23 of the incorporated patent which force 550 is applied to the resilient rearward member 482 of the lower member 480 of the lancet support member 460 (FIG. 23 of the incorporated patent) to advance the lancet 462 into engagement with a portion of a body to produce a body fluid.

Referring now particularly to FIGS. 7 and 8, the structure for advancing the lancet 462 in the alternate embodiment optical analyzer 110 different from the lancet advancing structure in the earlier embodiment optical analyzer 10 shown in FIGS. 2 and 3 will be described in detail; such structure resides within the housing 12.

Optical analyzer 110 includes an arming cylinder 112 mounted rotatably in the housing 12 by suitable means not shown but which means are within the skill of those of ordinary skill in the art, and which arming cylinder 112 is provided at its leftward end with a spur gear 114 for rotation therewith. A drive cylinder 116 is further included and which drive cylinder 116 is also mounted rotatably in the housing 12 by suitable means not shown but which means are also within the skill of one of ordinary skill in the art; the drive cylinder 116 is provided at its rightward end with a spur gear 115 for rotation therewith and which spur gear 116 is enmeshed with spur gear 114. The drive cylinder 116 is provided at its leftward end with a nutator plate 118 for rotation therewith.

A pivotally mounted bell crank 120 is further provided within the housing 12 and which bell crank 120 is mounted pivotally at point 122 in the housing 12 as shown in FIGS. 7 and 8. Bell crank 120 is provided at its upper end with a bias spring 121 having its rightward end connected to the housing 12 as shown and having its leftward end connected to the top portion of the bell crank 120 as shown. Bias spring 121 biases the bell crank 120 clockwise as shown by the arrow 123 in FIG. 7. A primary drive rod 124 having its leftward end mounted pivotally to the mid-portion of the bell crank 120 is also provided. Clockwise biasing of the bell crank 120 by the bias spring 123 forces the rightward end of the primary drive rod 124 into engagement with the nutator plate 118 as is also shown in FIG. 7. A secondary drive rod 126 is further provided and it will be understood as shown in FIGS. 7 and 8 that the rightward end of the secondary drive rod 126 is mounted pivotally to the upper portion of the bell crank 120 and the leftward end of the secondary drive rod 126 is positioned opposite the rearward end of the lancet 462 and more particularly positioned for engagement with the resilient rearward portion 482 of the lower member 480.

A torsion spring indicated by general numerical designation 130 surrounds the drive cylinder 116 with the rightward end thereof connected to the housing 12 at 131 as shown in FIGS. 7 and 8 and with the leftward end thereof connected at 132 as shown in FIGS. 7 and 8 to the rearward portion of the nutator plate 118. A manually operable pushbutton 136 is mounted slidably by suitable means not shown, but which means are within the skill of one of ordinary skill in the art, for inward movement into the housing 12 in the direction of the arrow 137. As shown in FIGS. 7 and 8, the inward end 138 of the pushbutton 136 is mounted pivotally to the upper end of a latch pawl 140 which latch pawl 140 is mounted pivotally to the housing 12 at 141, and the lower end of the latch pawl 140 is biased into engagement with the nutator plate 118 by a bias spring 142 having its leftward end connected to the lower portion of the latch pawl 140 and its rightward end connected to the housing 112. Bias spring 142 biases the latch pawl 140 in the counterclockwise direction as indicated by the arrow 143 in FIG. 7. The nutator plate 118 is provided with an inwardly extending recess 146 for receiving the lower portion of the latch pawl 140 to latch the nutator plate 118, and thereby drive cylinder 116 in a first position of rotation as illustrated in FIG. 7.

With regard to the gear ratio between the spur gears 114 and 115 mounted respectively on the leftward and rightward ends of the arming cylinder 112 and the drive cylinder 116, it will be understood that this ratio is such that upon an operator rotating the arming knob 160 provided on the rightward end of the arming cylinder 116 in the clockwise direction as indicated by the arrow 151 at the rightward portion of FIG. 7 a predetermined number of degrees as desired for convenience of operation, the drive cylinder 116 will be rotated in the counterclockwise direction as indicated by the arrow 153 in FIG. 7 180° to rotate the drive cylinder 116 and the nutator plate 118 from the normal or unlatched position shown in FIG. 8 into the latched or armed position shown in FIG. 7; such counterclockwise rotation of the drive cylinder 116 and the nutator plate 118 winds the torsion spring 130 to store energy for later advancement of the lancet 462 as described below. It will be understood that upon the presentment of the inwardly extending recess 146 formed in the cylindrical surface of the nutator plate 118, the lower end of the latch pawl 140, under the influence of the bias spring 142, drops or is forced into the recess to latch the nutator plate 118 and the drive cylinder 116 into the latched or armed position of rotation shown in FIG. 7.

In operation, it will be assumed that the structure of the optical analyzer 110 occupies the armed position illustrated in FIG. 7 and described above, that the disposable combined cuvette and lancet 410 shown in FIG. 22 of incorporated U.S. Pat. No. 4,873,393 has been removably received in the optical analyzer 110 with the lower member 480 of the combined cuvette and lancet 410 occupying the position shown therefor in FIG. 7 with the resilient rearward portion 482 and the lancet 462 occupying the positions therefor shown in FIG. 7. The operator will then depress the pushbutton 136 inwardly to rotate the latch pawl 140 in the clockwise direction as indicated by the arrow 157 in FIG. 8 to pivot the lower portion of the latch pawl 140 out of the recess 146 formed in the nutator plate 118 whereupon the nutator plate 118 and drive cylinder 116 will be released or unlatched. Thereupon, the previously wound torsion spring 130 will unwind or expand leftwardly as indicated by the arrow 158 in FIG. 8 which will cause the drive cylinder 116 and nutator plate 146 to rotate in the clockwise direction (as indicated by the circular arrow 161 in FIG. 8) from the position shown in FIG. 7 into the position shown in FIG. 8. Such clockwise rotation of the nutator plate 119 into the position shown in FIG. 8 advances the primary drive rod 124 leftwardly as also indicated by the arrow 158 which in turn pivots the bell crank 120 in the counterclockwise direction as indicated by the arrow 163 in FIG. 8 which in turn advances the secondary drive rod 126 leftwardly, also in the direction of the arrow 158 of FIG. 8, to cause the leftward end of the secondary drive rod 126 to engage the resilient rearward portion 482 of the lower member 480 (FIG. 8) which in turn advances the lancet 462, particularly the lancet tip 468, leftward in the direction of the arrow 158 to cause the lancet tip 468 to engage, for example, the finger of a person to puncture the finger and produce a drop of blood.

Thereafter, as taught above with regard to the optical analyzer embodiment 10 of FIGS. 1-6, the drop of blood is placed in the cuvette 420 shown in FIG. 22 of incorporated U.S. Pat. No. 4,873,393, and the photoemitter 34 and photodetector 36, computer 22 and display 24 of FIG. 2, operate as described above to produce a visible display indicative of the blood glucose level in the drop of blood produced by the above-described puncture by the lancet tip 468.

It will be understood by those skilled in the art that many variations and modifications may be made in the present invention without departing from the spirit and the scope thereof.

What is claimed is:

1. Optical analyzer for determining an analyte in a body fluid of interest, comprising:
   housing means;
   a combination optically transparent cuvette and lancet mounted removably in said housing means, said cuvette for receiving an optically transparent reagent test system for reacting with said body fluid to produce a change in at least one optical transmissive characteristic of said system indicative of said analyte;
   advancing means for advancing said lancet out of said housing and into engagement with a portion of a body to produce said body fluid;
   depth control means for controlling the depth of penetration of said lancet into said body portion;
   electro-optical means mounted in said housing means in optical engagement with said cuvette and for passing a light beam through said cuvette and said reagent system and for receiving said light beam modified by said change in optical transmissive characteristic of said system and for transmitting computation signals indicative of said analyte to computation means;
   computation means mounted in said housing means for receiving said computation signals and for comparing said computation signals against predetermined data to produce display signals indicative of said analyte;
   display means mounted in said housing means and for receiving said display signals and for providing a visible display indicative of said analyte;
   control means mounted in said housing means and connected to said computation means for controlling the operation of said computation means; and
   said advancing means including a spring rotated drive cylinder mounted rotatably in said housing means and having forward and rearward ends, said forward end of said drive cylinder provided with a nutator plate for rotating with said drive cylinder, a pivotally mounted bell crank, a primary drive rod having forward and rearward ends, said forward end of said primary drive rod mounted pivotally to said bell crank and said rearward end of said primary drive rod in engagement with said nutator plate, a first bias spring having forward and rearward ends, said rearward end of said first bias spring connected to said housing means and said forward end of said first bias spring connected to said bell crank and said first bias spring for biasing said bell crank towards said nutator plate to maintain said rearward end of said primary drive rod in engagement with said nutator plate, a secondary drive rod having forward and rearward ends, said rearward end of said secondary drive rod mounted pivotally to said bell crank and said forward end of said secondary drive rod positioned opposite said rearward end of said lancet, upon rotation of said drive cylinder said nutator plate advances said primary drive rod to pivot said bell rank which advances said secondary drive rod to cause said forward end of said secondary drive rod to advance said lancet into said engagement with said portion of said body to produce said body fluid.

2. The optical analyzer according to claim 1 wherein said advancing means comprise:
   cuvette carrier means mounted slidably in said housing means and for receiving said cuvette; and
   spring means mounted in said housing and connected to said cuvette carrier means, said spring means for being compressed and released to advance said carrier and thereby advance said lancet into engagement with a portion of a body to produce said body fluid.

3. The optical analyzer according to claim 1 wherein said regent test system reacts with said body fluid at a rate of reaction, wherein said corresponding change in at least one optical transmissive characteristic has a rate of change, wherein said light beam is modified at a rate of modification, and wherein said computation means determine the rate of change of said reaction from said received computation signals and compares the same against stored rates of change to determine said analyte and produce said display signs indicative thereof.

4. The optical analyzer according to claim 1 wherein said advancing means further includes a torsion spring wound around said drive cylinder, said torsion spring having forward and rearward ends, said forward end of said torsion spring connected to said nutator plate and said rearward end of said torsion spring connected to said housing means, an arming cylinder mounted rotatably in said housing means and having forward and rearward ends, said forward end of said drive cylinder positioned adjacent said rearward end of said drive cylinder, said rearward end of said drive cylinder and said forward end of said arming cylinder provided with enmeshed spur gears for rotating said drive cylinder and nutator plate to wind said torsion spring upon rotation of said arming cylinder, said rearward end of said arming cylinder provided with an arming knob for manual rotation by a person operating said optical analyzer, and manually operable push button means mounted in said housing for latching said nutator plate in a first position of rotation upon the winding of said torsion spring and for releasing said nutator plate to permit said wound torsion spring to unwind and rotate said nutator plate to advance said lancet.

5. The optical analyzer according to claim 4 wherein said push button means comprises a push button mounted in said housing means for inward movement thereinto, said push button having an inward end, a pivotally mounted latch pawl having first and second ends, said first end mounted pivotally to said inward end of said push button and said second end of said latch pawl in engagement with said nutator plate, a second bias spring having first and second ends, said first end of said second bias spring connected to said housing and said second end of said second bias spring connected to said second end of said latch pawl and for biasing said said second end of said latch pawl into engagement with said nutator plate, and wherein said nutator plate is provided with a recess for receiving said second end of said latch pawl to latch said nutator plate in said first position of rotation upon said nutator plate being rotated by said arming cylinder and said recess being presented opposite said second end of said latch pawl.

* * * * *